United States Patent
Sugiyama et al.

(10) Patent No.: US 6,258,233 B1
(45) Date of Patent: Jul. 10, 2001

(54) MULTILAYERED AIR-FUEL RATIO SENSING ELEMENT

(75) Inventors: Tomio Sugiyama, Nagoya; Masahiro Shibata, deceased, late of Nagoya, by Midori Shibata, Natsumi Shibata, Raina Shibata, legal representatives; Hiromi Sano, Nagoya, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/237,918

(22) Filed: Jan. 27, 1999

Related U.S. Application Data

(63) Continuation-in-part of application No. 08/993,406, filed on Dec. 18, 1997, now abandoned, which is a continuation of application No. 08/678,821, filed on Jul. 12, 1996, now abandoned.

(30) Foreign Application Priority Data

| Jul. 13, 1995 | (JP) | 7-201522 |
| Mar. 5, 1998 | (JP) | 10-073584 |
| Oct. 15, 1998 | (JP) | 10-293814 |

(51) Int. Cl.[7] .................. G01N 27/409; G01N 27/41; C04B 35/48

(52) U.S. Cl. .................. 204/424; 501/103; 501/134; 501/152

(58) Field of Search .................. 204/424, 425, 204/426, 427, 428, 429; 510/103, 134, 152

(56) References Cited

U.S. PATENT DOCUMENTS

| 4,219,359 | 8/1980 | Miwa et al. | 501/135 |
| 4,266,979 * | 5/1981 | Miyoshi et al. | 501/103 |
| 4,328,296 * | 5/1982 | Tanaka et al. | 429/193 |
| 4,344,904 * | 8/1982 | Yamada et al. | 264/66 |
| 4,360,598 * | 11/1982 | Otagiri et al. | 501/103 |
| 4,370,393 * | 1/1983 | Watanabe et al. | 429/193 |
| 4,505,807 | 3/1985 | Yamada | 204/425 |
| 4,724,061 | 2/1988 | Nyberg | 204/412 |
| 4,866,014 * | 9/1989 | Cassidy et al. | 501/103 |
| 5,130,002 * | 7/1992 | Murase et al. | 204/425 |
| 5,169,513 | 12/1992 | Mase et al. | 204/429 |
| 5,447,618 * | 9/1995 | Sugiyama et al. | 204/426 |
| 5,518,603 | 5/1996 | Furuhashi et al. | 204/429 |

FOREIGN PATENT DOCUMENTS

| 2 087 569 | 5/1982 | (GB) . |
| 57-82761 | 5/1982 | (JP) . |
| 59-41952 | 10/1984 | (JP) . |
| 60-259952 | 12/1985 | (JP) . |

* cited by examiner

Primary Examiner—Robert J. Warden, Sr.
Assistant Examiner—Kaj K. Olsen
(74) Attorney, Agent, or Firm—Pillsbury Winthrop LLP

(57) ABSTRACT

A multilayered air-fuel ratio sensing element has a zirconic solid electrolytic body and a heat-generating portion including an alumina substrate located adjacent to the zirconic solid electrolytic body. The zirconic solid electrolytic body is made of a partially stabilized zirconia containing 5~7 mol % yttria and having a mixed phase structure including a cubic phase, a monoclinic phase and a tetragonal phase. The zirconic solid electrolytic body has a relative density of 94~100% with a mean sintered grain size $R_{ZR}$ of 0.5~3.0 μm. The alumina substrate has a relative density of 95~100% with a mean sintered grain size $R_{AL}$ of 0.5~4.0 μm. And, the partially stabilized zirconia has an M/C ratio in a range from 0.05 to 0.25.

4 Claims, 13 Drawing Sheets

MULTILAYERED AIR-FUEL RATIO SENSING ELEMENT

CROSS REFERENCE TO RELATED APPLICATION

This application is continuation-in-part of the applicant's pending U.S. application "Laminated Oxygen-sensor Device Comprising A Solid Electrolyte Member Made Of Partially Stabilized Zirconia" Ser. No. 08/993,406, filed Dec. 18, 1997 (now abandoned), which is a continuation of U.S. application Ser. No. 08/678,821, filed on Jul. 12, 1996 (now abandoned).

BACKGROUND OF THE INVENTION

The present invention relates to a multilayered air-fuel ratio sensing element preferably used for the air-fuel ratio control of internal combustion engines for automotive vehicles.

From the recent trend toward shortened sensor activation time and the positional restriction in installing the sensor (for example, installation to the exhaust gas pipe under a vehicle floor panel), improvement of the sensor warmup ability as well as downsizing of the sensor body are important goals to be attained.

Multilayered air-fuel ratio sensing elements, including united sensing and heating portions, have prospective properties to satisfy these requirements.

From the view point of electric insulation and heat transfer, conventionally proposed multilayered air-fuel ratio sensing elements generally comprise a heater-equipped alumina substrate and an oxygen ion conductive solid electrolytic body which are laminated integrally and sintered together. As having sufficient strength and excellent oxygen ionic conductivity, the partially stabilized zirconia is generally used as the oxygen ion conductive solid electrolytic body.

However, the multilayered air-fuel sensing elements have the following drawbacks because of their structural features including the different members (i.e., alumina and partially stabilized zirconia). When the sensing element is sintered in the manufacturing process or heated in the actual operating environment, a significant amount of thermal stress concentrates at the boundary between the alumina and the partially stabilized zirconia due to thermal expansion difference between them. This thermal stress triggers the cracks.

Enhancing the composition of the partially stabilized zirconia as well as increasing the strength and controlling the thickness of the alumina substrate will be effective to suppress the cracks from generating during the sintering step for manufacturing the sensing element from laminated green sheets of the alumina substrate and the solid electrolytic body (refer to the U.S. Pat. No. 5,447,618).

However, when the multilayered air-fuel ratio sensing element is installed in the internal combustion engine of an automotive vehicle, cracks may appear by the following mechanism.

The partially stabilized zirconic solid electrolytic body has a mixed phase structure including three different crystal structures referred to as a cubic (C) phase, a monoclinic (M) phase and a tetragonal (T) phase, with a small amount of additives. According to this phase structure, the T phase can transform into the M phase through the isothermal martensitic transformation (refer to T→M transformation).

The T→M transformation progresses rapidly when the partially stabilized zirconia is exposed to an atmosphere of approximately 200° C. Presence of water (e.g., moisture or vapor) promotes the T→M transformation. Furthermore, the T→M transformation causes a volumetric change.

The operating environment of the air-fuel ratio sensing element incorporated in the automotive internal combustion engine can be regarded as repetitive heating and cooling cycles in a temperature range from the room temperature (20° C.) to the exhaust gas temperature (1,000° C.). The exhaust gas contains a large amount of vapor. Under such environment, the T→M transformation progresses smoothly.

When the T→M transformation occurs in the solid electrolytic body, cracks will appear along the boundary between the solid electrolytic body and the alumina substrate or along the surface of the solid electrolytic body.

SUMMARY OF THE INVENTION

In view of the foregoing problems encountered in the prior art, the present invention has an object to provide a multilayered air-fuel ratio sensing element causing no cracks even when it is subjected to severe heating and cooling cycles under a high humid environment.

In order to accomplish the above-described and other related objects, the present invention provides a multilayered air-fuel ratio sensing element comprising a zirconic solid electrolytic body and a heat-generating portion, wherein the zirconic solid electrolytic body is made of a partially stabilized zirconia containing 5~7 mol % yttria and having a mixed phase structure including a cubic (C) phase, a monoclinic (M) phase and a tetragonal (T) phase. The zirconic solid electrolytic body has a relative density of 94~100%, with a mean sintered grain size $R_{ZR}$ of 0.5~3.0 μm. The heat-generating portion includes an alumina substrate which is located adjacent to the zirconic solid electrolytic body and has a relative density of 95~100% with a mean sintered grain size $R_{AL}$ of 0.5~4.0 μm. And, the partially stabilized zirconia has an M/C ratio in a range from 0.05 to 0.25. The M/C ratio is defined by the following equation:

$$\frac{M}{C} = \frac{M(111) + M(11\bar{1})}{M(111) + M(11\bar{1}) + C(111)}$$

wherein $M(11\bar{1})$ represents a reflective integrated intensity of a monoclinic phase($11\bar{1}$); M(111) represents a reflective integrated intensity of a monoclinic phase (111); and C(111) represents a reflective integrated intensity of a cubic phase (111).

The zirconic solid electrolytic body is made of the partially stabilized zirconia. When the yttria content in the partially stabilized zirconia is out of the range of 5~7 mol %, the thermal expansion difference between the zirconic solid electrolytic body and the alumina substrate increases, while causing a stress acting on the alumina substrate. Thus, cracks appear on the alumina substrate.

When the relative density of the zirconic solid electrolytic body is in a range from 0 to 94%, the zirconic solid electrolytic body may loose gas tightness (i.e., may have poor gas permeability).

As described later, to detect an air-fuel ratio of the measuring gas, the zirconic solid electrolytic body is provided with at least a pair of electrodes. One of the paired electrodes is exposed to the measuring gas, while the other electrode is exposed to the reference gas. When the solid electrolytic body is not gas tight, the measuring gas may mix with the reference gas. In this case, the air-fuel ratio cannot be measured accurately.

Furthermore, the solid electrolytic body will be deteriorated in strength.

In view of strength and ionic conductivity, it is preferable that the allowable upper limit of the relative density is 100%.

When the mean sintered grain size $R_{ZR}$ of the zirconic solid electrolytic body is in a range from 0 to 0.5 μm, it is difficult in the manufacturing of the zirconic solid electrolytic body to attain the relative density of 94% or more even if the industrially obtainable finest material is used. Thus, a gas tight and strong zirconic solid electrolytic body cannot be obtained.

When the mean sintered grain size $R_{ZR}$ exceeds 3.0 μm, a large volumetric change occurs in accordance with the T→M transformation of the T-phase crystal particles in the sintered body. The produced internal stress may concentrate at the grain boundary, causing cracks in the solid electrolytic body.

When the relative density of the alumina substrate is in a range from 0 to 95%, the alumina substrate will be deteriorated in strength. A thermal stress derived from the thermal expansion difference between the alumina substrate and the zirconic solid electrolytic body will cause cracks.

In view of electric insulation, it is preferable that the allowable upper limit of the relative density is 100%.

When the mean sintered grain size $R_{AL}$ of the alumina substrate exceeds 4.0 μm, cracks may appear when the alumina substrate is subjected to repetitive heating and cooling cycles.

Although the reasons are not clear, it is generally assumed that a thermal stress derived from the thermal expansion difference concentrates at the boundary between the zirconia and the alumina when there is a large difference in the mean sintered grain size between the zirconia and the alumina. This develops fine cracks.

When the mean sintered grain size $R_{AL}$ is in a range from 0 to 0.5 μm, it is difficult in the manufacturing of the alumina substrate to attain the relative density of 95% or more even if the industrially obtainable finest material is used. Thus, the alumina substrate will deteriorate in strength. Under heating and cooling cycles, a thermal stress derived from the thermal expansion difference between the alumina substrate and the zirconic solid electrolytic body will cause cracks.

The present invention has the following functions and effects.

As described above, the multilayered air-fuel ratio sensing element of the present invention comprises the solid electrolytic body made of a partially stabilized zirconia and the heat-generating portion including an alumina substrate located adjacent to the solid electrolytic body.

The partially stabilized zirconia contains 5~7 mol % yttria and has a mixed phase structure including the C phase having a thermal expansion coefficient of approximately $11 \times 10^{-6}/°$ C., the T phase having a thermal expansion coefficient of approximately $9 \times 10^{-6}/°$ C., and the M phase having a thermal expansion coefficient of approximately $4 \times 10^{-6}/°$ C. Furthermore, the partially stabilized zirconia has an M/C ratio in a range from 0.05 to 0.25.

According to the present invention, there is a small thermal expansion difference between the solid electrolytic body and the alumina substrate (having a thermal expansion coefficient of approximately $8 \times 10^{-6}/°$ C.). Thus, the generation of the cracks can be effectively suppressed.

When the M/C ratio is smaller than 0.05 or larger than 0.25, there will be a large difference in the thermal expansion coefficient between the solid electrolytic body and the alumina substrate. The large thermal expansion difference induces a large thermal stress with cracks appearing on the alumina substrate or on the solid electrolytic body or at their boundary.

Furthermore, when the M/C ratio of the partially stabilized zirconia is in the range from 0.05 to 0.25, the yttria content is approximately 4.5~6.5 mol. FIG. 18 shows the transformation of this partially stabilized zirconia.

As apparent from FIG. 18, when the M/C ratio is set to the range defined by the present invention, the M→T transformation occurs in accordance with a temperature increase so that the mixed crystal of the M phase and the C phase transforms into the mixed crystal of the T phase and the C phase. A volumetric change also occurs.

Especially, the T→M transformation occurs in response to a reduction of temperature. However, the actual transformation does not change all of the T phase into the M phase because part of the T phase is restrained by the surrounding stable C phase. In other words, part of the T phase is frozen in the C phase at the room temperature.

When the amount of the frozen T phase is constant, i.e., when the T phase is stably restrained by the C phase, the M/C ratio can be stably maintained even if the partially stabilized zirconia is subjected to repetitive heating and cooling cycles. Thus, it becomes possible to suppress the generation of cracks.

However, a restraining force acting from the C phase to the T phase varies depending on the grain size of the T phase. More specifically, a greater grain size promotes the T→M transformation, allowing the T phase to separate from the C phase.

When the mean sintered grain size $R_{ZR}$ of the zirconic solid electrolytic body exceeds 3.0 μm, the transformation force of the T phase exceeds the freezing force of the C phase acting on the T phase. Thus, it becomes difficult to stably freeze the T phase in the C phase at the room temperature.

As a result, when the zirconic solid electrolytic body is subjected to repetitive heating and cooling cycles, the amount of the T phase frozen in the C phase at the room temperature gradually changes. The M/C ratio changes correspondingly. This leads to the change in the thermal expansion coefficient. The cracks appear on the solid electrolytic body.

As described above, the present invention limits the mean sintered grain size of the zirconic solid electrolytic body in the above-described range. With this setting, the M/C ratio of the partially stabilized zirconia can be stably maintained even if the partially stabilized zirconia is subjected to the repetitive heating and cooling cycles.

Furthermore, when each relative density of the zirconic solid electrolytic body and the alumina substrate is in the above-described range, the strength can be enhanced. This is effective to suppress the generation of cracks.

Moreover, as the multilayered air-fuel ratio sensing element of the present invention has the excellent crystallographic stability as described above, no cracks appear even when it is subjected to the repetitive heating and cooling cycles under a high humid environment, e.g., in a vapor-containing gas atmosphere.

As described above, the present invention makes it possible to provide a multilayered air-fuel ratio sensing element causing no cracks even when it is subjected to severe heating and cooling cycles under a high humid environment.

Furthermore, it is preferable that a thermal expansion difference A between the alumina substrate and the partially stabilized zirconia is in a range from 0 to 0.2. The thermal expansion difference A is defined by the following equation:

$$\Delta = \frac{C_{ZR} \cdot T - C_{AL} \cdot T}{1 + C_{AL} \cdot T} \times 100(\%)$$

wherein $C_{ZR}$ represents a thermal expansion coefficient of the partially stabilized zirconia in a temperature range from the room temperature (20° C.) to 1,000° C.; CAL represents a thermal expansion coefficient of the alumina in a temperature range from the room temperature (20° C.) to 1,000° C.; and T represents a temperature variation (980° C.).

With this setting, it becomes possible to suppress the thermal stress arising between the partially stabilized zirconia and the alumina even when the element is subjected to the repetitive heating and cooling cycles in the temperature range from the room temperature (20° C.) to 1,000° C. The generation of cracks can be effectively suppressed.

Needless to say, it is preferable that the thermal expansion difference between the partially stabilized zirconia and the alumina is completely eliminated. In this case, no thermal stress arises.

When the thermal expansion difference exceeds 0.2, a large thermal stress will arise between the partially stabilized zirconia and the alumina, causing the cracks.

Furthermore, it is preferable that the ratio of the mean sintered grain size $R_{AL}$ of the alumina substrate to the mean sintered grain size $R_{ZR}$ of the zirconic solid electrolytic body is in a range from 0.33 to 4.00, i.e., $0.33 \leq R_{AL}/R_{ZR} \leq 4.00$.

With this setting, it becomes possible to suppress the generation of cracks even when the thermal stress arises due to the thermal expansion difference.

When the ratio $R_{AL}/R_{ZR}$ is smaller than 0.33, the zirconic solid electrolytic body will contain a large amount of yttria. This increases the thermal expansion difference between the zirconic solid electrolytic body and the alumina substrate. The cracks will appear on the element. On the other hand, when the ratio $R_{AL}/R_{ZR}$ is larger than 4.00, the alumina substrate has a large value in the mean sintered grain size with a reduced strength. Thus, the material strength will be insufficient against the thermal stress arising due to the thermal expansion difference. The cracks will appear on the element.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Figure 1:
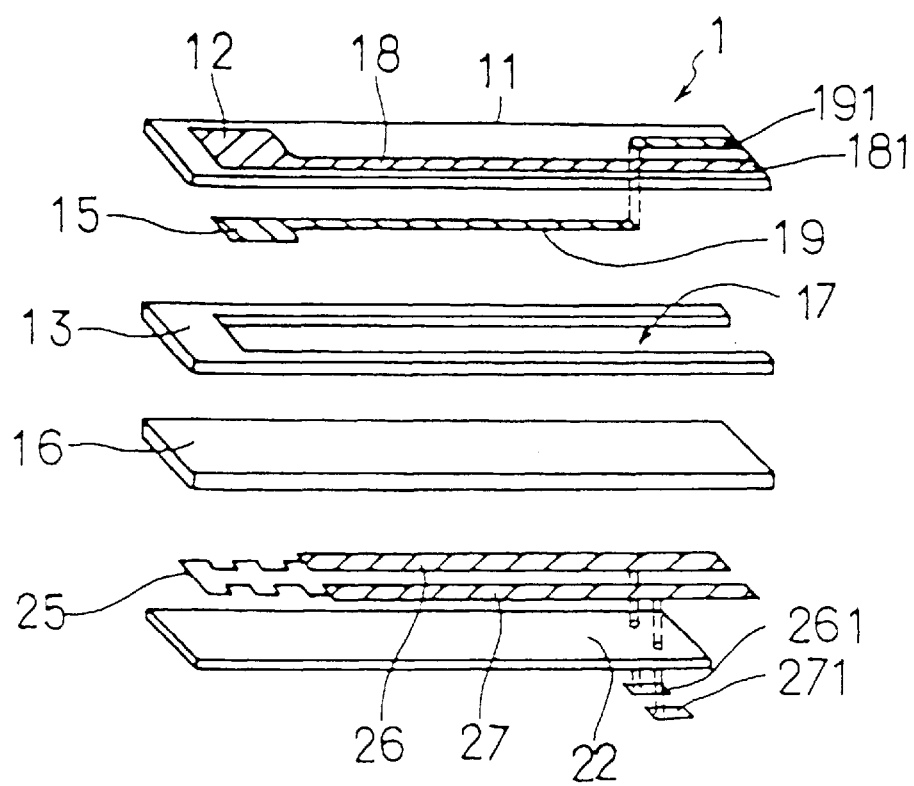
FIG. 1 is a perspective exploded view showing a multilayered air-fuel ratio sensing element in accordance with a preferred embodiment of the present invention.

Preferred embodiments of the present invention will be explained hereinafter with reference to accompanied drawings. Identical parts are denoted by the same reference numerals throughout the drawings.

Multilayered air-fuel ratio sensing elements in accordance with a preferred embodiment of the present invention will be explained with reference to FIGS. 1 to 7.

Figure 2:
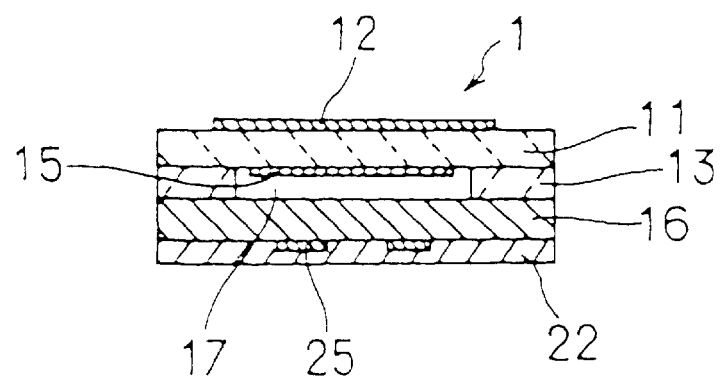
FIG. 2 is a cross-sectional view showing the multilayered air-fuel ratio sensing element in accordance with the preferred embodiment of the present invention.

As shown in FIGS. 1 and 2, a multilayered air-fuel ratio sensing element 1 comprises a zirconic solid electrolytic body 11 and a heat-generating portion equipped with a heater 25. The heat-generating portion comprises a plurality of alumina substrate 22, 16, and 13 stacked in this order. The alumina substrate 13 is located adjacent to the zirconic solid electrolytic body 11.

The zirconic solid electrolytic body 11 is made of a partially stabilized zirconia containing 5~7 mol % yttria and having a mixed phase structure including a cubic (C) phase, a monoclinic (M) phase and a tetragonal (T) phase.

The zirconic solid electrolytic body 11 has a relative density of 94~100%, with a mean sintered grain size $R_{ZR}$ of 0.5~3.0 μm.

The alumina substrate 13, located adjacent to the zirconic solid electrolytic body 11, has a relative density of 95~100% with a mean sintered grain size $R_{AL}$ of 0.5~4.0 μm. And, the partially stabilized zirconia has an M/C ratio in a range from 0.05 to 0.25. The M/C ratio is defined by the following equation (1):

$$\frac{M}{C} = \frac{M(111) + M(11\bar{1})}{M(111) + <(11\bar{1}) + C(111)} \quad (1)$$

wherein $M(11\bar{1})$ represents a reflective integrated intensity of a monoclinic phase $(11\bar{1})$; $M(111)$ represents a reflective integrated intensity of a monoclinic phase (111); and C(111) represents a reflective integrated intensity of a cubic phase (111).

Next, the detailed arrangement of the multilayered air-fuel ratio sensing element 1 in accordance with the preferred embodiment will be explained.

As shown in FIGS. 1 and 2, the multilayered air-fuel ratio sensing element 1 comprises the zirconic solid electrolytic body 11 and the heat-generating portion equipped with the heater 25. The heat-generating portion includes the alumina substrate 13 located adjacent to the zirconic solid electrolytic body 11.

A measuring electrode 12, provided on an outer surface of the zirconic solid electrolytic body 11, is electrically connected to a signal output terminal 181 via a lead 18 both provided on the same surface (upper or outer surface) of the zirconic solid electrolytic body 11. A reference electrode 15, provided on an opposite surface (lower or inner surface) of the zirconic solid electrolytic body 11, is electrically connected to a signal output terminal 191 provided on the upper or outer surface via a lead 19 extending along the lower or inner surface of the zirconic solid electrolytic body 11, as shown in FIGS. 1 and 2.

The zirconic solid electrolytic body 11 is laminated or stacked on the alumina substrate 13. The alumina substrate 13 has a U-shaped configuration to provide a gas passage 17 extending in the longitudinal direction for introducing air serving as a reference gas. The gas passage 17 serves as a reference gas chamber. The reference electrode 15 is exposed to the reference gas introduced in the gas passage 17.

The heater 25, interposed between the alumina substrates 16 and 22, is electrically connected to power supply terminals 261 and 271 via leads 26 and 27 extending on the same surface.

The manufacturing method of the multilayered air-fuel ratio sensing element 1 will be described, hereinafter.

First, a zirconia powder having a mean grain size of 0.5 μm and a yttria powder having a mean grain size of 0.5 μm are mixed to provide a weighed body including 6 mol % yttria. Then, the resultant weighed body (100 weight part) is mixed with an organic solvent together with a binder and a plasticizer in a ball mill for 24 hours, to obtain a slurry. The organic solvent is a mixture of ethanol (10 weight part) and toluene (10 weight part). The binder is polyvinyl butyral (5 weight part). The plasticizer is dibutyl phthalate (10 weight part).

Next, the slurry is configured into a green sheet by using the doctor blade method to obtain a green zirconic sheet having a thickness of 0.2 mm in a dried condition. The green zirconic sheet is cut into a rectangular shape of 5 mm×70 mm. A vertical through hole is opened across the sheet to electrically connect the reference electrode 15 to the signal output terminal 191 via the lead 19.

Next, a zirconia-containing Pt paste is applied on the surfaces of the green zirconic sheet by the screen printing method to form the print pattern of the measuring electrode 12, the reference electrode 15, the leads 18 and 19, and the signal output terminals 181 and 191. Thus, a green sheet of the zirconic solid electrolytic body 11 is obtained.

Separately, prepared is a mixture of α-alumina (97 weight part) having a mean grain size of 0.3 μm, partially stabilized zirconia (3 weight part) containing 6 mol % yttria, PVB (10 weight part), DBP (10 weight part), ethanol (30 weight part), and toluene (30 weight part). From this mixture, another slurry is obtained through a 24-hour processing in the ball mill.

The obtained slurry is configured into a green sheet by using the doctor blade method to obtain a green alumina sheet having a thickness of 1.0 mm in a dried condition. The green alumina sheet is cut into a rectangular shape of 5 mm×70 mm, thereby obtaining a green sheet of the alumina substrate 16. The green alumina sheet is also cut into a U-shape configuration of 5 mm×70 mm in the outer periphery with the cutout of 2 mm×67 mm, thereby obtaining a green sheet of the alumina substrate 13.

A green sheet of the alumina substrate 22 is obtained by using the same material and the same method as those of the green sheet of the alumina substrate 16. The green sheet of the alumina substrate 22 has a thickness of 0.2 mm in a dried condition and a size of 5 mm×70 mm.

Furthermore, two through holes are opened across the green sheet of the alumina substrate 22 at the end thereof to electrically connect the leads 26 and 27 to the power supply terminals 261 and 271, respectively.

Next, an alumina-containing paste is applied on the surfaces of the green sheet of the alumina substrate 22 by the screen printing method to form the print pattern of the heater 25, the leads 26 and 27, and the power supply terminals 261 and 271.

The green sheets thus obtained are laminated or put one on another in a manner shown in FIG. 1, and united by the thermal press processing. Then, the resultant laminated body is sintered at 1,475° C. for two hours to obtain the multilayered air-fuel ratio sensing element 1.

Next, the zirconic solid electrolytic body, constituting the multilayered air-fuel ratio sensing element 1, is subjected to a test to measure and evaluate its performance in comparison with comparative samples.

First, several test pieces were fabricated to evaluate the relative density, the mean sintered grain size, and a thermal expansion difference between the alumina and zirconia sheets.

A total of ten green zirconic sheets for the zirconic solid electrolytic body 11 were fabricated according to the above-described manufacturing method. Two green alumina sheets for the alumina substrates 13, 16 and 22 were fabricated according to the above-described manufacturing method. These green sheets were subjected to the thermal press processing and sintered under the same conditions as those of the above-described manufacturing method. The resultant sintered body was cut into a test piece of 1.6 mm×5.0 mm×50 mm. Then, a specific gravity of the test piece was measured in the water. By comparing the specific gravity in the water and the specific gravity in the air (true specific gravity), the relative density was calculated.

Next, the cut surface of the test piece was soaked into a 10% hydrofluoric acid solution for 30 minutes. Thereafter, the mean sintered grain size was measured by taking an SEM photograph.

Figure 3:
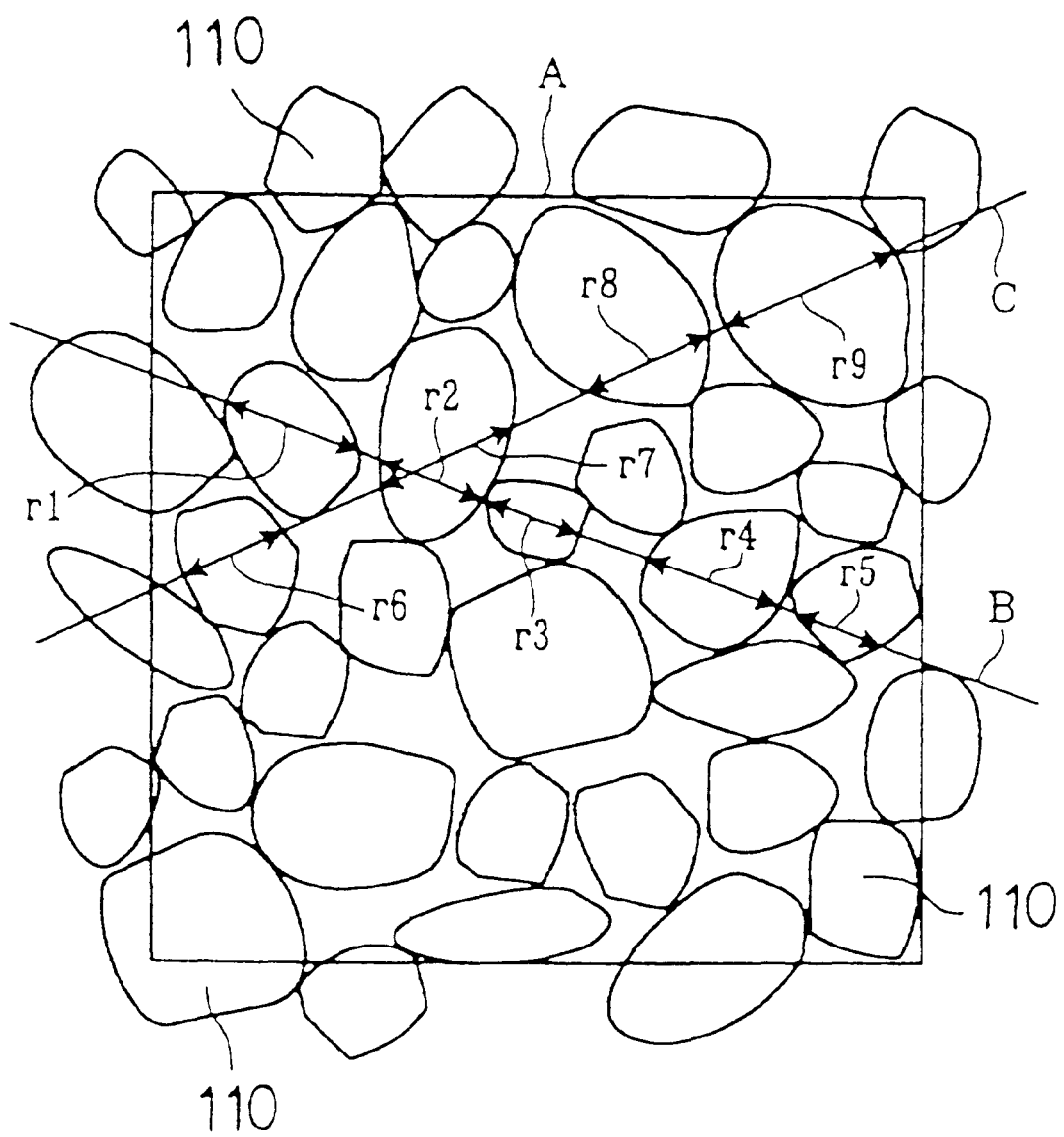
FIG. 3 is a view illustrating a method for measuring the mean sintered grain size in accordance with the preferred embodiment of the present invention.

FIG. 3 shows the method for measuring the mean sintered grain size, according to which straight lines "B" and "C" are arbitrarily drawn so as to cross a given square "A" of 20 μm×20 μm. When the straight line "B" or "C" crosses a crystal particle 110, the length of each overlapped portion is measured. Measured lengths r1, r2, r3, r4 and r5 were obtained from the overlapped relationship between the straight line "B" and the crystal particles 110 in the square "A." Other measured lengths r6, r7, r8, and r9 were obtained from the overlapped relationship between the straight line "C" and the crystal particles 110 in the square "A." The mean sintered grain size was obtained as a mean value of these overlap lengths r1 through r9.

Furthermore, the alumina sheet and the zirconia sheet were left in the air and their temperatures were increased from the room temperature (20° C.) to 1,000° C. The thermal expansions of these sheets were measured by using an appropriate thermal expansion meter. Then, the thermal expansion difference Δ was calculated based on the following equation (2).

$$\Delta = \frac{50 \times (1 + C_{ZR} \cdot 980) - 50 \times (1 + C_{AL} \cdot 980)}{50 \times (1 + C_{AL} \cdot 980)} \times 100 \quad (2)$$

$$= \frac{C_{ZR} \cdot 980 - C_{AL} \cdot 980}{1 + C_{AL} \cdot 980} \times 100$$

50—length (mm) of test piece at room temperature;
980—temperature difference (° C.) between the room temperature (20° C.) and 1,000° C.;
$C_{zr}$—thermal expansion coefficient (1/° C.) of zirconia in the temperature range from the room temperature (20° C.) to 1,000° C.; and
$C_{al}$—thermal expansion coefficient (1/° C.) of alumina in the temperature range from the room temperature (20° C.) to 1,000° C.

From the measurement result, it was found that the zirconic test piece had a relative density of 97% with a mean sintered grain size of 1.0 μm. The alumina test piece had a relative density of 98% with a mean sintered grain size of 2.0 μm. The thermal expansion difference A between the zirconic test piece and the alumina test piece was 0.04.

Next, the zirconic test piece, crushed in advance, was further crushed into 150 mesh-level powders through a 10-minute grinding in an alumina mortar. Then, the M/C ratio defined by the equation (1) was measured by an appropriate X-ray diffraction apparatus. The measured M/C ratio was 0.16.

Next, the multilayered air-fuel ratio sensing element 1 was subjected to a thermal shock test.

In this thermal shock test, the multilayered air-fuel ratio sensing element 1 was subjected to the following repetitive heating and cooling cycles. Then, a dyeing test is applied to the element 1 to check the presence of cracks appearing on the surface of the element 1.

The heating operation is performed by supplying electric power to the heater 25 of the element 1 so that the temperature of the measuring electrode 12 or its vicinity increases 1,000° C. in 20 seconds. Subsequently, the element 1 is forcibly cooled down from the 1,000° C. to the room temperature (20° C.) in 100 seconds. The heating and cooling cycles are repeated in an environment having a relative humidity of 70%.

The dyeing test revealed that the multilayered air-fuel ratio sensing element 1 caused no crack even after 50,000 heating and cooling cycles.

Then, to check the stability against water, the multilayered air-fuel ratio sensing element 1 was subjected to an autoclave test at 200° C. This test utilizes the fact that the T-M transformation progresses rapidly at about 200° C. under the presence of hot water.

After finishing the autoclave heating, the presence of any crack on the element 1 was checked by the dyeing test.

As a result, it was confirmed that the multilayered air-fuel ratio sensing element 1 caused no crack.

As described above, the multilayered air-fuel ratio sensing element of the preferred embodiment is a united element comprising different members, i.e., the alumina substrate and the zirconic electrolytic body made of a partially stabilized zirconia. However, the above-described various test results reveal that the multilayered air-fuel ratio sensing element of the preferred embodiment is durable against the severe "heating and cooling cycles under a high humid atmosphere" similar to the actual operating environment.

The preferred embodiment of the present invention has the following functions and effects.

The multilayered air-fuel ratio sensing element 1 of the preferred embodiment comprises the solid electrolytic body 11 made of a partially stabilized zirconia and the heat-generating portion equipped with the heater 25. The heat-generating portion comprises the alumina substrate 13 located adjacent to the solid electrolytic body 11.

The partially stabilized zirconia contains 5~7 mol % yttria, with a mixed phase structure including the C phase having a thermal expansion coefficient of approximately $11 \times 10^{-6}/°$ C., the T phase having a thermal expansion coefficient of approximately $9 \times 10^{-6}/°$ C., and the M phase having a thermal expansion coefficient of approximately $4 \times 10^{-6}/°$ C. Furthermore, the M/C ratio of the partially stabilized zirconia is in the range from 0.05 to 0.25.

Accordingly, there is a small difference in the thermal expansion between the solid electrolytic body 11 and the alumina substrate 13 (having a thermal expansion coefficient of approximately $8 \times 10^{-6}/°$ C.). The small thermal expansion difference produces a small thermal stress between the two members, causing no cracks.

Furthermore, the zirconic solid electrolytic body 11 and the alumina substrate 13 have the above-described mean sintered grain sizes. This is effective to prevent the crystal particles, existing as T phase, from causing volumetric changes by the existence of neighboring stable C phase. The volumetric chance, even if it occurs, is small with a small stress.

The stress, when induced by the T→M transformation, may concentrate at the grain boundary between the alumina and the zirconia. However, the direction of the crack is changed in various directions by the grain boundary, thereby effectively suppressing the development of cracks.

Furthermore, the zirconic solid electrolytic body 11 and the alumina substrate 13 have the above-described relative densities. This is effective to enhance the strength of the element 1 so as to suppress the generation of cracks.

Furthermore, the multilayered air-fuel ratio sensing element 1 of the preferred embodiment has the above-described crystallographic stability. This is effective to prevent the element 1 from generating cracks even if it is subjected to the repetitive heating and cooling cycles under the humid environment, e.g., in the vapor-containing gas atmosphere.

As described above, the preferred embodiment provides a multilayered air-fuel ratio sensing element causing no cracks even when it is subjected to severe heating and cooling cycles under a high humid environment.

Figure 4:
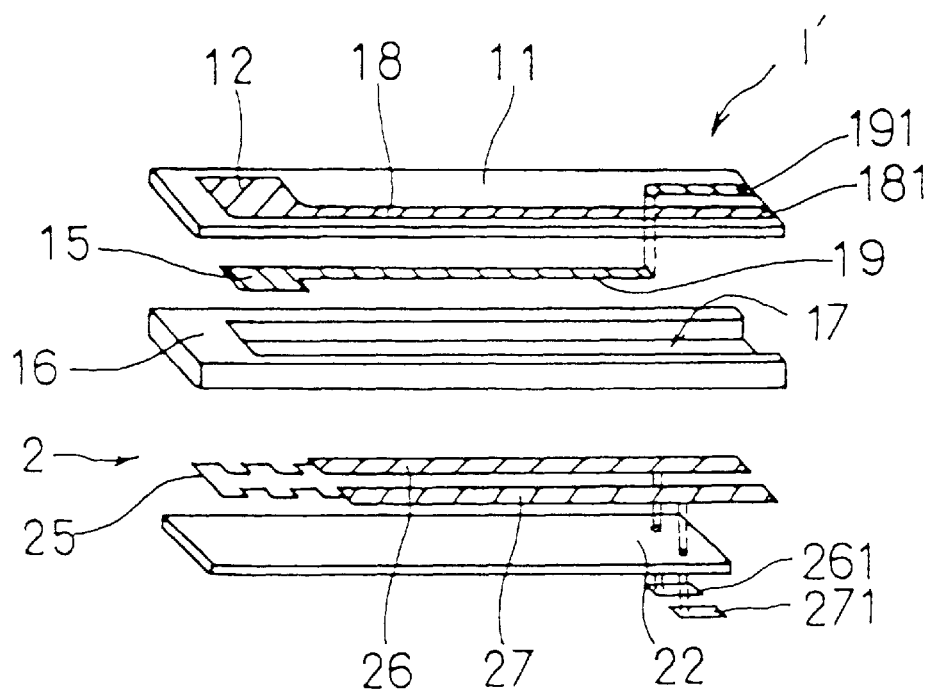
FIG. 4 is a perspective exploded view showing another multilayered air-fuel ratio sensing element in accordance with the preferred embodiment of the present invention.
Figure 5:
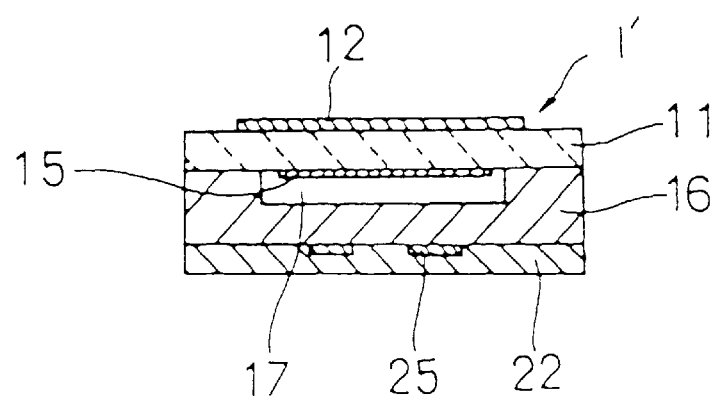
FIG. 5 is a cross-sectional view showing the multilayered air-fuel ratio sensing element shown in FIG. 4.

FIGS. 4 and 5 show a modified multilayered air-fuel ratio sensing element 1' in accordance with the preferred embodiment of the present invention. The sensing element 1' shown in FIGS. 4 and 5 differs from the sensing element 1 shown in FIGS. 1 and 2 in that the heat-generating portion includes two alumina substrates 22 and 16 stacked in this order. More specifically, the alumina substrate 16 is located adjacent to the zirconic solid electrolytic body 11, and the gas passage (i.e., gas chamber) 17 is provided in the alumina substrate 16.

According to this modified embodiment, it becomes possible to simplify the manufacturing processes because the multilayered air-fuel ratio sensing element 1' has a reduced number of alumina substrates. Furthermore, airtightness is improved. The increased portion shared by the alumina leads to the enhancement of the strength of the sensing element 1'. Other functions and effects are similar to those of the above-described sensing element 1.

Figure 6:
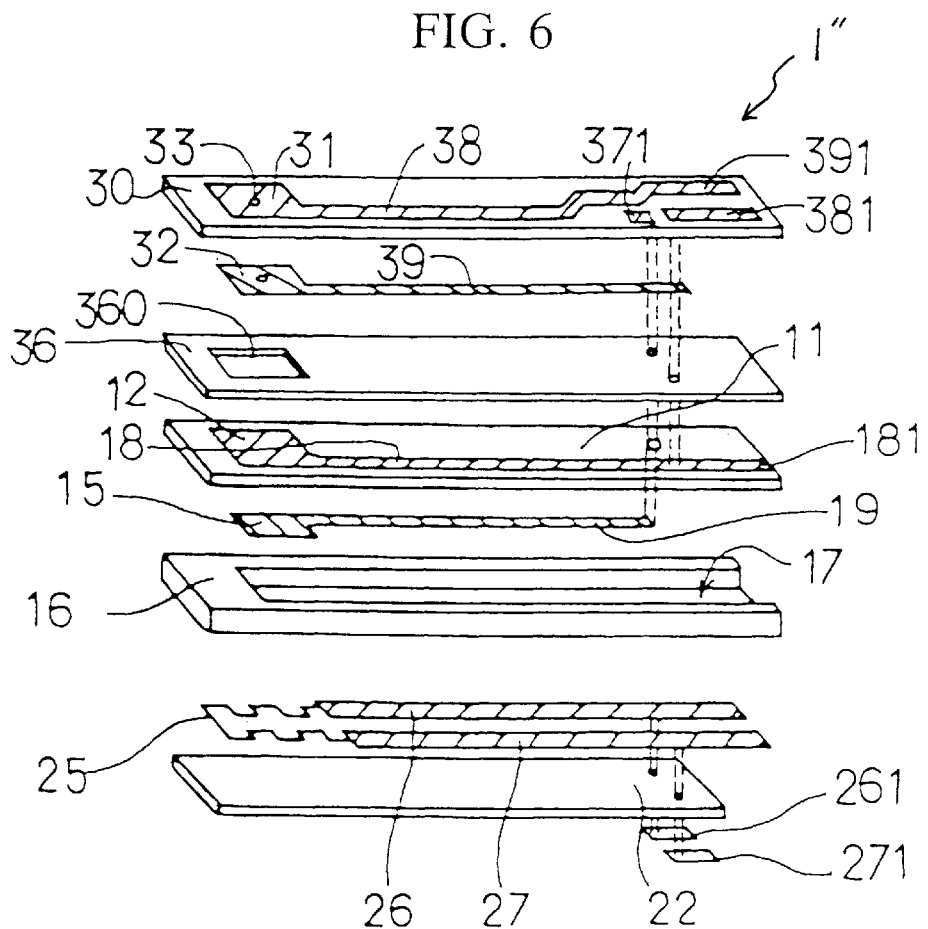
FIG. 6 is a perspective exploded view showing another multilayered air-fuel ratio sensing element having a pump cell in accordance with the preferred embodiment of the present invention.
Figure 7:
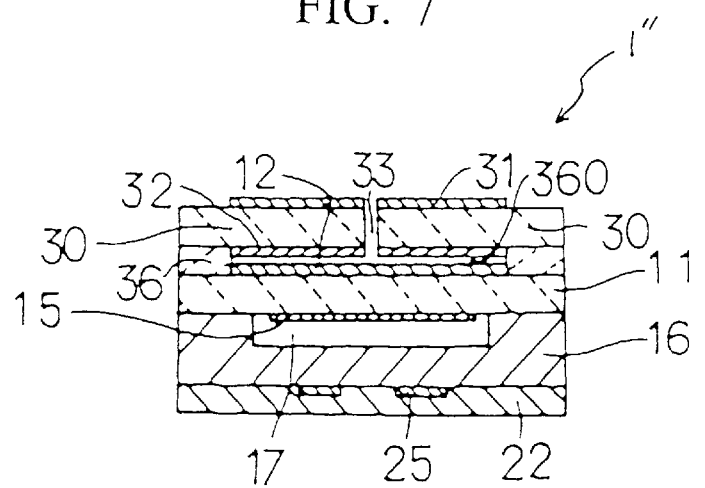
FIG. 7 is a cross-sectional view showing the multilayered air-fuel ratio sensing element shown in FIG. 6.

Furthermore, FIGS. 6 and 7 show another modified multilayered air-fuel ratio sensing element 1" in accordance with the preferred embodiment of the present invention. According to this modified embodiment, the multilayered air-fuel ratio sensing element 1" comprises the zirconic solid electrolytic element 11 and the heat-generating portion equipped with the heater 25. The heat-generating portion includes two alumina substrates 22 and 16 stacked in this order. The alumina substrate 16 is located adjacent to the zirconic solid electrolytic body 11, and the gas passage (i.e., gas chamber) 17 is provided in the alumina substrate 16.

A measuring gas chamber forming plate 36 and a pump cell substrate 30 are provided at the opposite side of the zirconic solid electrolytic element 11.

The pump cell substrate 30 has a pair of pump electrodes 31 and 32 provided on opposite surfaces thereof. To introduce the measuring gas into a measuring gas chamber, a pin hole 33 extends across the pump cell substrate 30 from the center of the pump electrode 31 to the center of the pump electrode 32. A window 360 of the measuring gas chamber forming plate 36 serves as the measuring gas chamber. The window 360 faces to the measuring electrode 12.

The pump cell substrate 30 has leads 38 and 39 extending along the surfaces thereof and electrically connected to the pump electrodes 31 and 32 at one end and to voltage applying terminals 391 and 381 at the other end, respectively. A signal output terminal 371 is also provided for the reference electrode 15. The terminals 371 and 381 are electrically connected to the lead 19 and the terminal 181 formed on the surfaces of the zirconic solid electrolytic body 11 via through holes.

The multilayered air-fuel ratio sensing element 1" shown in FIGS. 6 and 7 can measure a wide range of air-fuel ratio and is, therefore, preferably used for controlling the internal combustion engine so as to realize a precise air-fuel ratio adjustment. Other functions and effects are similar to those of the above-described sensing elements 1 and 1'.

FIGS. 8 through 17 show evaluations of various samples having the same shapes and manufactured in the same manner by the same materials as those of the multilayered air-fuel ratio sensing elements disclosed in the above-described preferred embodiment. To evaluation the performance, the samples were subjected to the tests similar to those disclosed in the preferred embodiment.

First, using the method similar to that disclosed in the preferred embodiment, zirconia and yttria powders both having a mean grain size of 0.1, 0.5, or 1.0 $\mu$m were mixed to provide various weighed bodies each including 4.5, 5.0, 5.5. 6.0, 6.5, 7.0, or 7.5 mol % yttria. The obtained weighed bodies are formed into slurries which are used to fabricate zirconic test pieces by using the method disclosed in the preferred embodiment.

Figure 8:
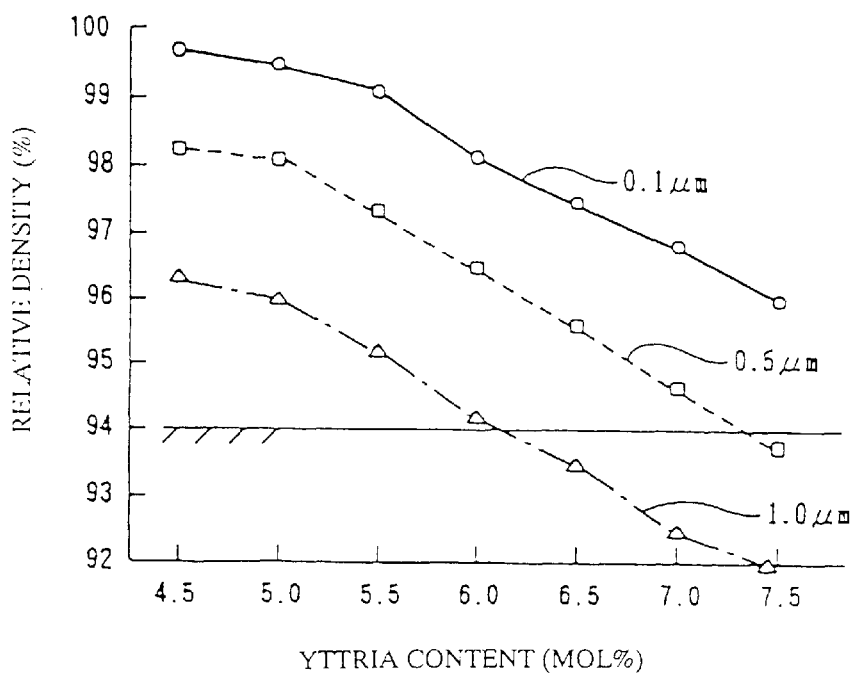
FIG. 8 is a graph showing a relationship between the relative density and the yttria content in the zirconia test pieces in accordance with the present invention.
Figure 9:
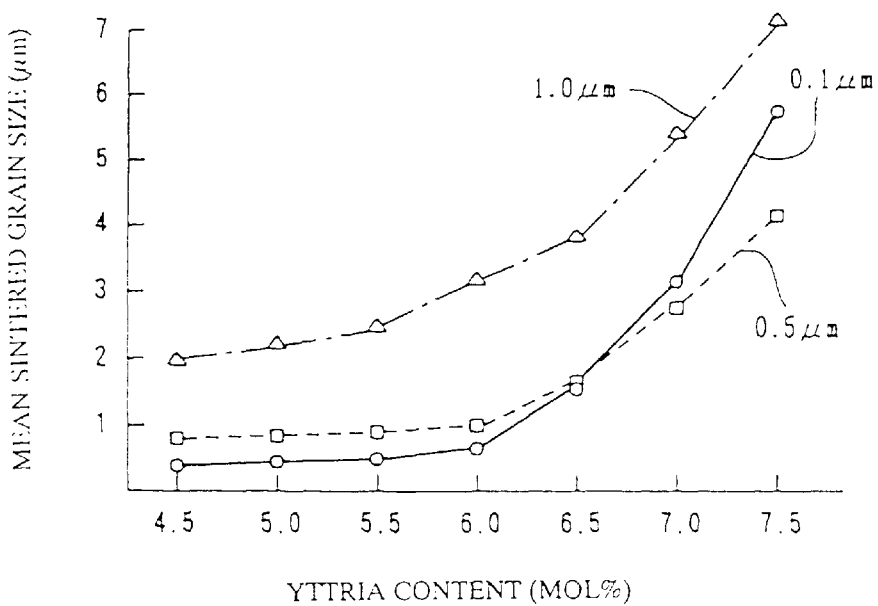
FIG. 9 is a graph showing a relationship between the mean sintered grain size and the yttria content in the zirconia test pieces in accordance with the present invention.

FIG. 8 shows the relationship between the relative density of each zirconic test piece and the yttria content (mol %), measured in the same manner as disclosed in the preferred embodiment. FIG. 9 shows the relationship between the mean sintered grain size of each zirconic test piece and the yttria content (mol %), measured in the same manner as disclosed in the preferred embodiment.

The test result shown in FIG. 8 reveals that the relative density decreases with increasing yttria content (mol %) and that the relative density is higher when the material grain size is small. It is also found that more than 94% in the relative density can be attained only when the yttria content (mol %) and the material grain size are adequately selected.

Furthermore, FIG. 9 reveals that the mean sintered grain size increases with increasing yttria content (mol %).

On the other hand, by using the method similar to that disclosed in the preferred embodiment, various alumina test pieces are fabricated from several alumina materials having mean grain sizes of 0.1, 0.3, and 0.7 $\mu$m.

Figure 10:
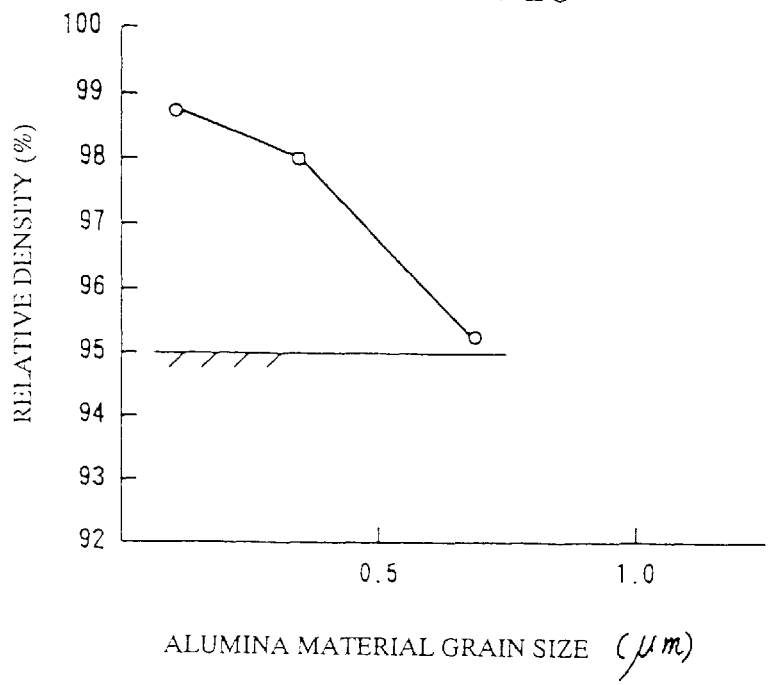
FIG. 10 is a graph showing a relationship between the alumina material grain size and the relative density in the resultant alumina test piece in accordance with the present invention.
Figure 11:
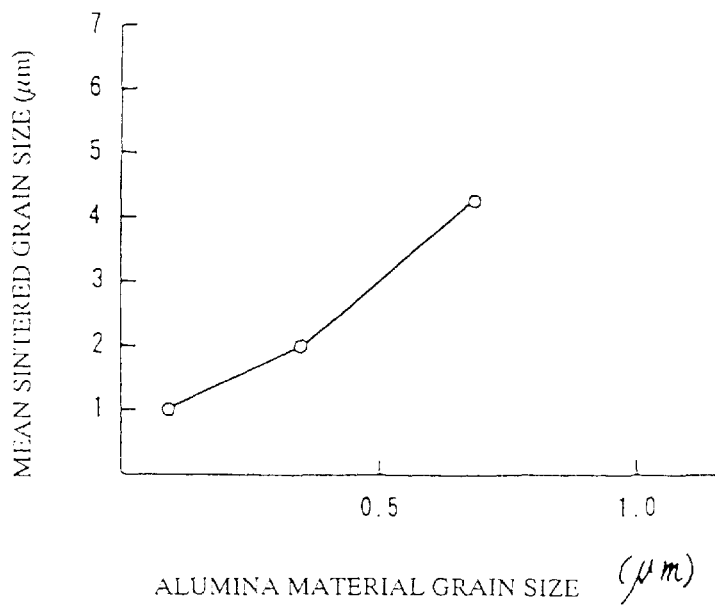
FIG. 11 is a graph showing a relationship between the material grain size and the mean sintered grain size of the alumina test pieces in accordance with the present invention.

FIG. 10 shows the relationship between the relative density of each alumina test piece and the alumina material grain size, measured in the same manner as disclosed in the preferred embodiment. FIG. 11 shows the relationship between the mean sintered grain size of alumina test piece and the alumina material grain size, measured in the same manner as disclosed in the preferred embodiment.

The test result of FIG. 10 reveals that the relative density decreases with increasing grain size of the alumina material. The test result of FIG. 11 reveals that the mean sintered grain size increases with increasing grain size of the alumina material.

Figure 12:
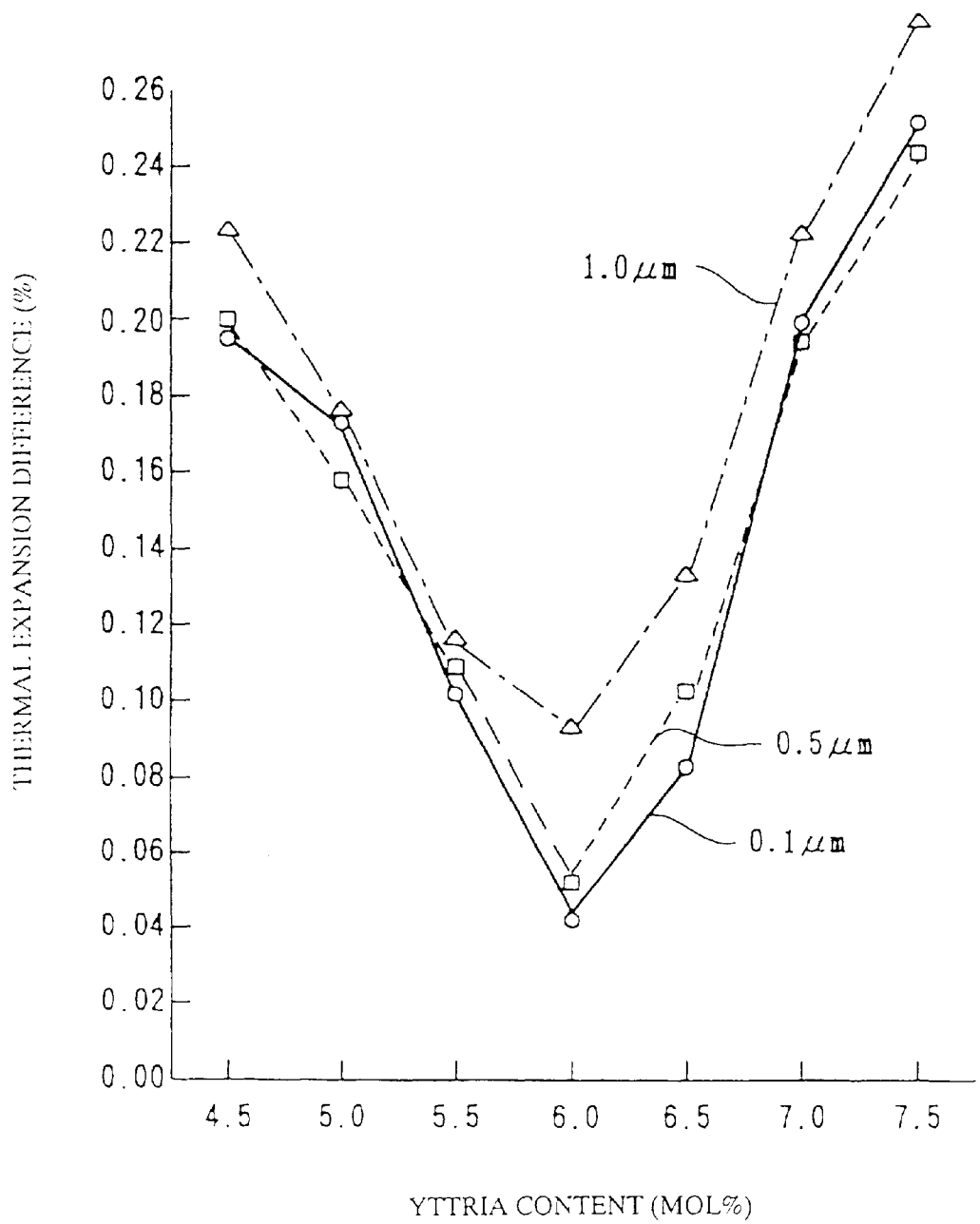
FIG. 12 is a graph showing a relationship between the yttria content in the zirconic solid electrolytic body and the thermal expansion difference in accordance with the present invention.

Furthermore, a thermal expansion coefficient of each zirconia test piece was measured by using an appropriate thermal expansion meter in the same manner as in the preferred embodiment. FIG. 12 shows the thermal expansion difference between each zirconia test piece and the alumina test piece having a relative density of 98% with a mean sintered grain size of 2 $\mu$m disclosed in the preferred embodiment.

Figure 13:
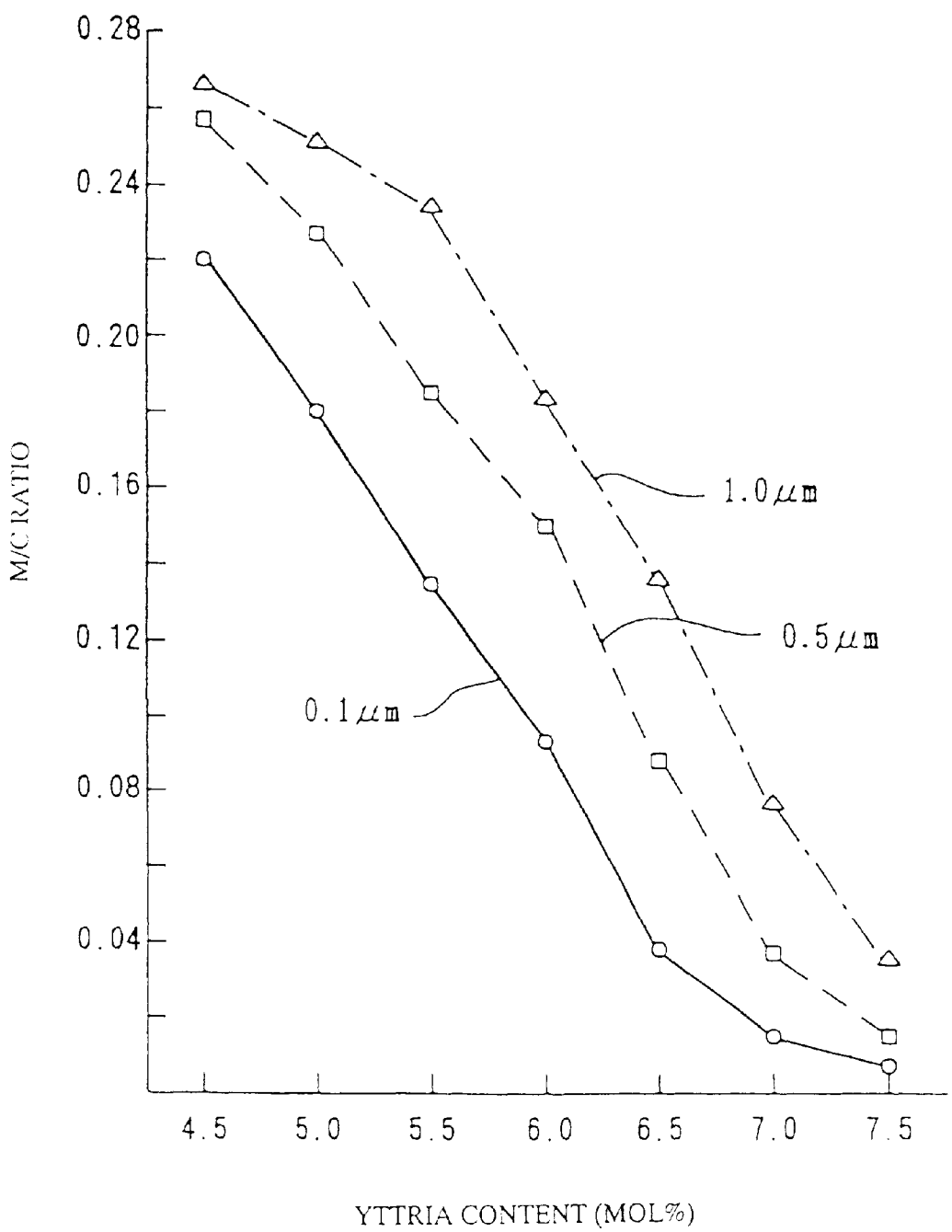
FIG. 13 is a graph showing a relationship between the yttria content in the zirconic solid electrolytic body and the M/C ratio in accordance with the present invention.

FIG. 13 shows the M/C ratio of each zirconia test piece measured in the same manner as in the preferred embodiment.

Next, using the slurries, the multilayered air-fuel ratio sensing elements were manufactured by the manufacturing method disclosed in the preferred embodiment (refer to FIGS. 1 and 2). Each of the resultant multilayered air-fuel ratio sensing elements was subjected to the thermal shock test in the same manner as disclosed in the preferred embodiment. Tables 1~3 show the measured result, wherein test samples marked by O remained normal but test samples marked by × caused cracks.

Figure 14:
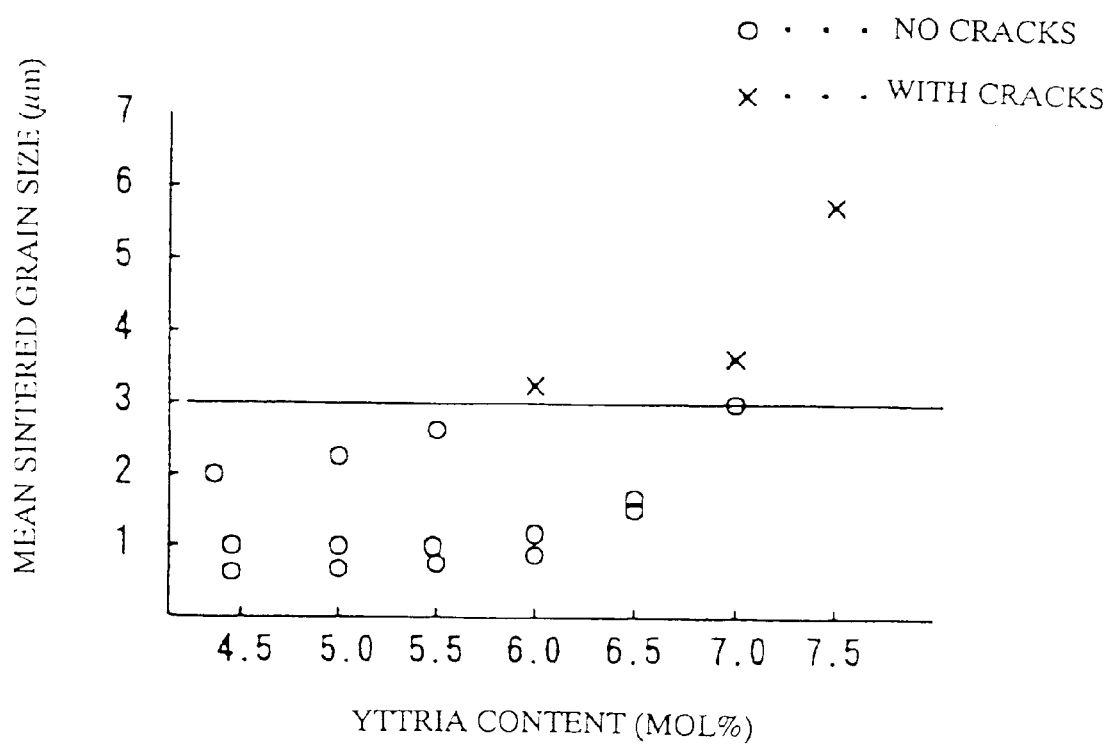
FIG. 14 is a graph showing a relationship between the yttria content in the zirconic solid electrolytic body and the mean sintered grain size in accordance with the present invention.

FIG. 14 summarizes the test result listed in tables 1~3 in relation to the mean sintered grain size and the yttria content (mol %). As apparent from the result shown in FIG. 14, it is confirmed that no crack appears when the mean sintered grain size of the zirconia is equal to or smaller than 3.0 $\mu$m.

Figure 15:
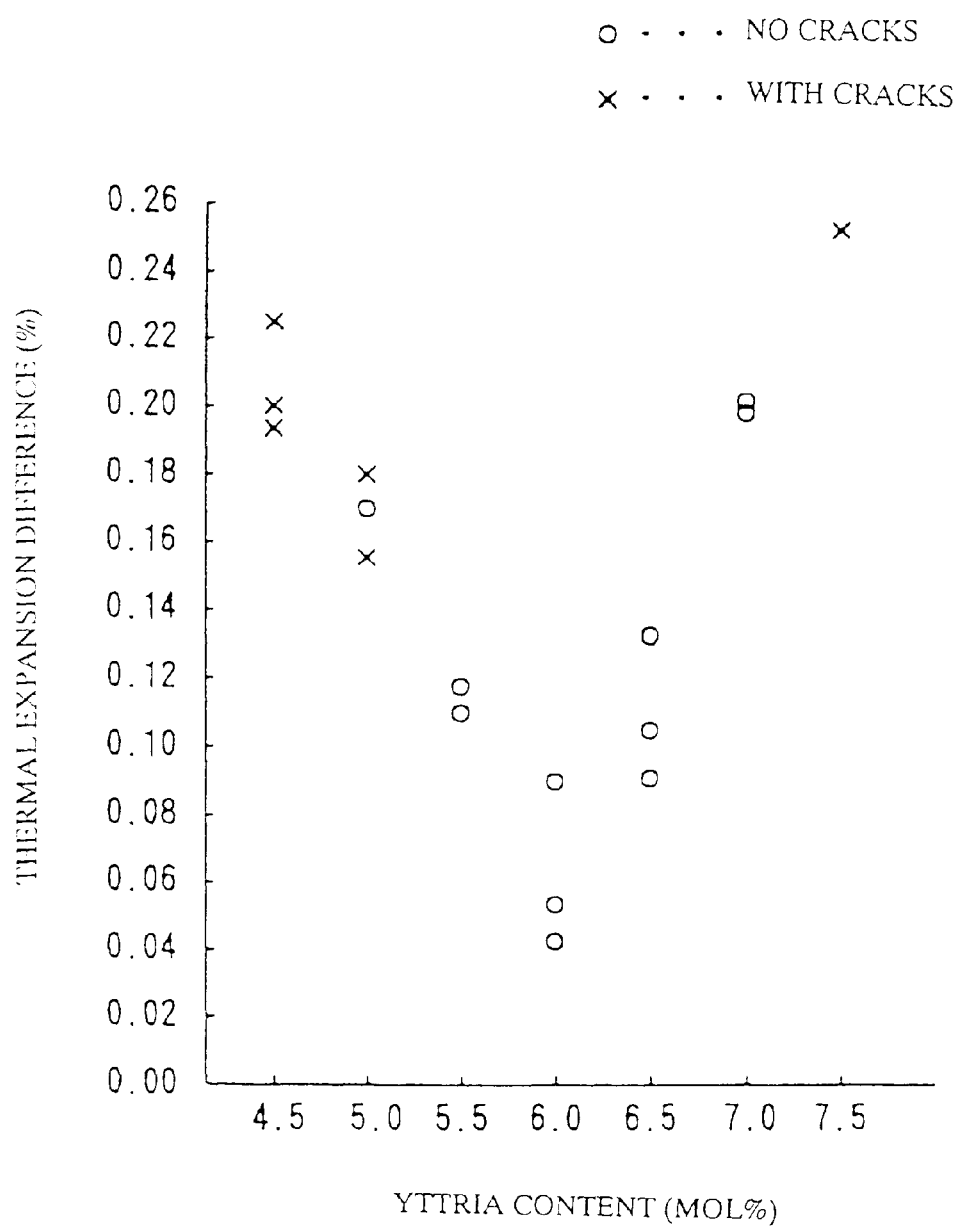
FIG. 15 is a graph showing a relationship between the yttria content in the zirconic solid electrolytic body and the thermal expansion difference in accordance with the present invention.

FIG. 15 summarizes the test result listed in tables 1~3 in relation to the thermal expansion difference (shown in FIG. 12) and the yttria content (mol %).

As apparent from the result shown in FIG. 15, it is confirmed that no crack appears when the thermal expansion difference between the alumina test piece and the zirconia test piece is equal to or smaller than 0.2% in the larger mol % region of the yttria content.

However, some cracks appear in the smaller mol % region of the yttria content even when the thermal expansion difference between the alumina test piece and the zirconia test piece is 0.16%. From the result of FIG. 13, the M/C ratio is large when the yttria content is small. Thus, it is believed that the large M/C ratio induces the cracks. The mean sintered grain size is small when the yttria content (mol %) is small. In the manufacturing of the element, there is a process for cooling the sintered element. During this cooling process, there is a tendency that the T phase is frozen in a polycrystalline substance. The presence of vapor or water induces the T-M transformation which causes a volumetric change. It is thus believed that the cracks appear due to such a volumetric change.

As shown in FIG. 15, the cracks appear when the thermal expansion difference between the alumina test piece and the zirconia test piece is larger than 0.20%. It is believed that the large thermal expansion difference between the alumina test piece and the zirconia test piece causes a large thermal stress which triggers the cracks.

Figure 16:
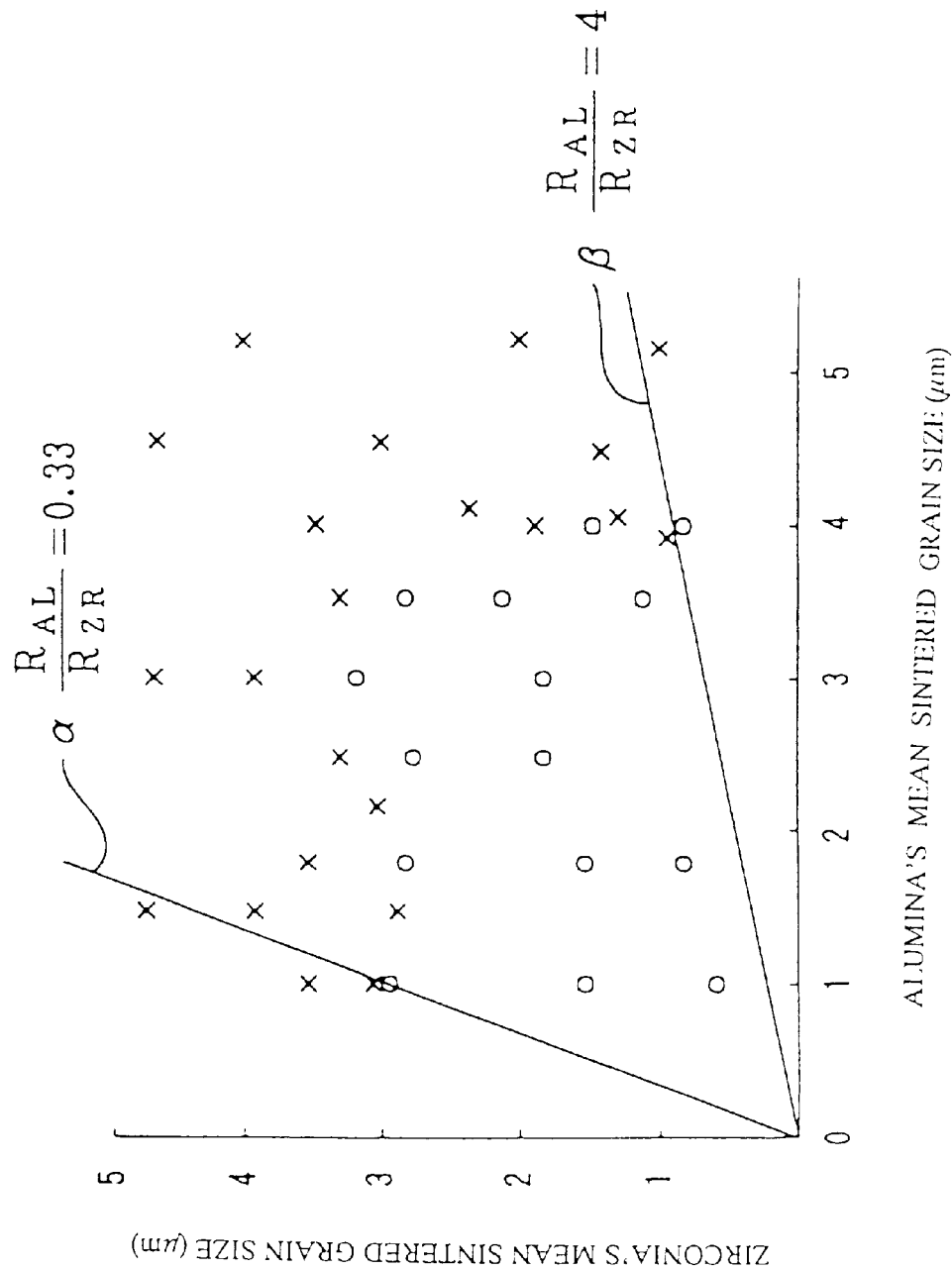
FIG. 16 is a graph showing a relationship in the mean sintered grain size between the zirconia and alumina test pieces in accordance with the present invention.

Next, the influence of the mean sintered grain sizes of the alumina and zirconia test pieces is checked with respect to the generation of cracks through the thermal shock test. The sintering temperatures of the above-described zirconia and alumina test pieces were set to 1,475° C., 1,525° C., and 1,575° C. The obtained test pieces were subjected to the above-described thermal shock test. FIG. 16 shows the relationship between the mean sintered grain sizes of the zirconia and alumina test pieces with respect to the crack generation.

Figure 17:
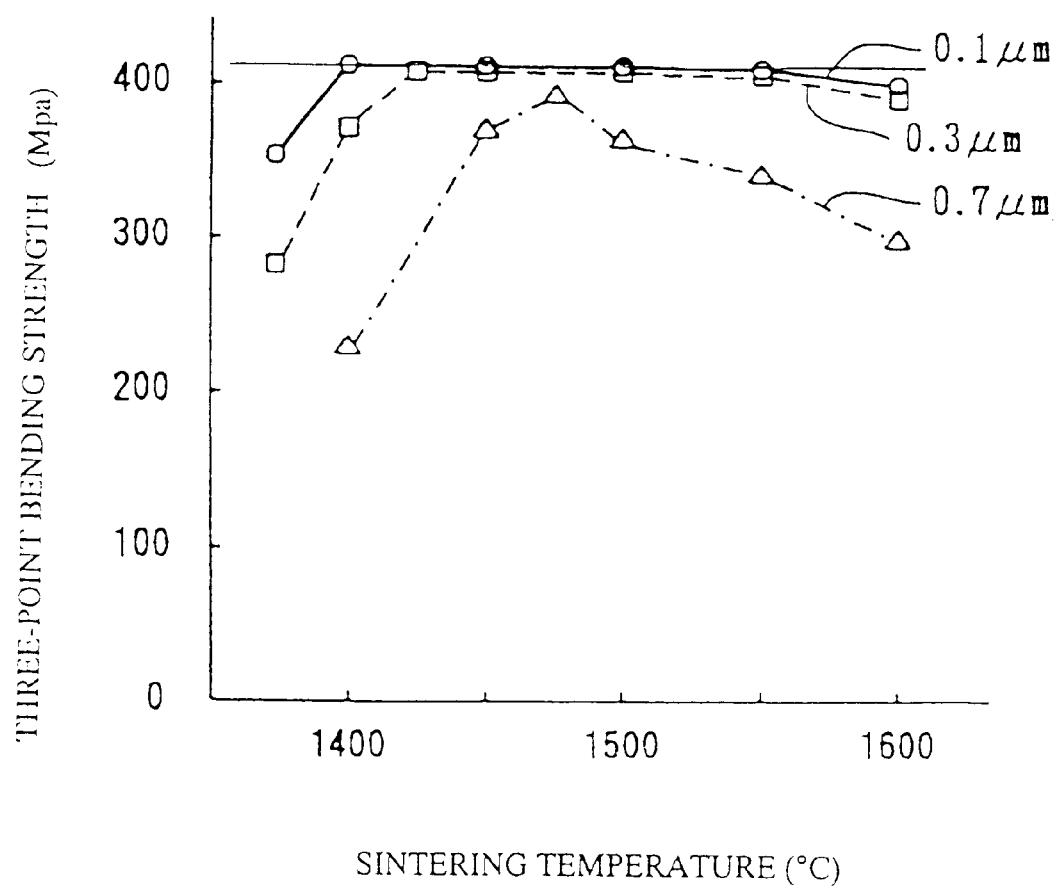
FIG. 17 is a graph showing a relationship between the sintering temperature and the three-point bending strength in respective alumina material grain sizes in accordance with the present invention.
Figure 18:
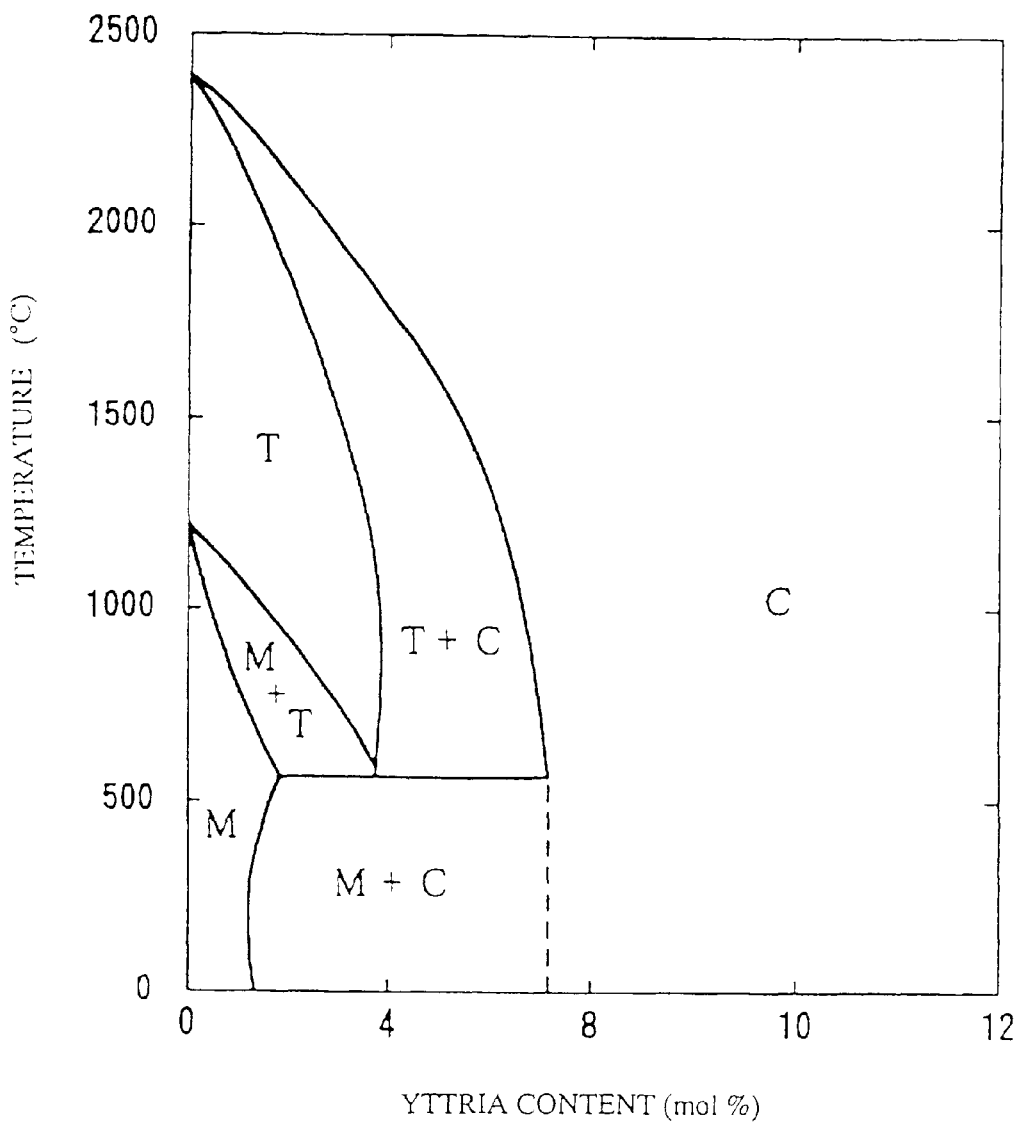
FIG. 18 is a graph showing the transformation of a partially stabilized zirconia.

Meanwhile, it is believed that the generation of cracks derived from the thermal expansion difference significantly depends on the strength of the alumina substrate. FIG. 17 shows the strength of each alumina test piece measured through a three-point bending test. In FIG. 17, numeral of each curve shows a mean grain size of the material used for manufacturing the alumina test piece.

The result of FIG. 16 reveals that the cracks appear when the mean sintered grain size of the alumina test piece exceeds 4.0 μm or when the mean sintered grain size of the zirconia test piece exceeds 3.0 μm.

The result of FIG. 17 reveals that the strength decreases with increasing material grain size. When the material grain size is large, the mean sintered grain size is large correspondingly. Accordingly, it is believed that the cracks appear when the mean sintered grain size of the alumina test piece exceeds 4.0 μm.

The cracks appear when the mean sintered grain size of the zirconic test piece exceeds 3.0 μm even when the alumina test piece has a small mean sintered grain size sufficient for assuring a sufficient strength. It is thus believed that the grain size ratio between the zirconic and alumina test pieces may give some influence to the generation of the cracks. Probably, it is assumed that a large grain size difference will induce cracks in response to a thermal stress caused by the thermal expansion difference.

As understood from FIG. 16, an optimum range in terms of the mean sintered grain size ratio $R_{AL}/R_{ZR}$ is from 0.33 to 4.00, as obtained from the straight lines α and β drawn in FIG. 16, wherein $R_{AL}$ and $R_{ZR}$ represent mean sintered grain sizes of the alumina and zirconic test pieces, respectively.

Although the above-described embodiments are explained based on the multilayered air-fuel ratio sensing elements, the present invention is applicable to any other sensing elements, such as a NOx sensor, an HC sensor, and a $CO_2$ sensor, which comprise both the alumina substrate and the partially stabilized zirconia.

TABLE 1

| Zirconia | | Alumina | | | | |
|---|---|---|---|---|---|---|
| Material grain size (μm) | Yttria (mol %) | Material grain size (μm) | Heating and cooling cycles (times) | | | |
| | | | 5,000 | 10,000 | 20,000 | 50,000 |
| 0.1 | 4.5 | 0.1 | ○ | ○ | x | x |
| | 5.0 | | ○ | ○ | ○ | ○ |
| | 5.5 | | ○ | ○ | ○ | ○ |
| | 6.0 | | ○ | ○ | ○ | ○ |
| | 6.5 | | ○ | ○ | ○ | ○ |
| | 7.0 | | ○ | ○ | x | x |
| | 7.5 | | x | x | x | x |
| 0.5 | 4.5 | | ○ | ○ | x | x |
| | 5.0 | | ○ | ○ | ○ | x |
| | 5.5 | | ○ | ○ | ○ | ○ |
| | 6.0 | | ○ | ○ | ○ | ○ |
| | 6.5 | | ○ | ○ | ○ | ○ |
| | 7.0 | | ○ | ○ | ○ | ○ |
| | 7.5 | | Zirconia has a low relative density | | | |
| 1.0 | 4.5 | | ○ | x | x | x |
| | 5.0 | | ○ | ○ | ○ | x |
| | 5.5 | | ○ | ○ | ○ | ○ |
| | 6.0 | | ○ | ○ | ○ | x |
| | 6.5 | | Zirconia has a low relative density | | | |
| | 7.0 | | | | | |
| | 7.5 | | | | | |

TABLE 2

| Zirconia | | Alumina | | | | |
|---|---|---|---|---|---|---|
| Material grain size (μm) | Yttria (mol %) | Material grain size (μm) | Heating and cooling cycles (times) | | | |
| | | | 5,000 | 10,000 | 20,000 | 50,000 |
| 0.1 | 4.5 | 0.3 | ○ | ○ | x | x |
| | 5.0 | | ○ | ○ | ○ | ○ |
| | 5.5 | | ○ | ○ | ○ | ○ |
| | 6.0 | | ○ | ○ | ○ | ○ |
| | 6.5 | | ○ | ○ | ○ | ○ |
| | 7.0 | | ○ | ○ | x | x |
| | 7.5 | | x | x | x | x |
| 0.5 | 4.5 | | ○ | ○ | x | x |
| | 5.0 | | ○ | ○ | ○ | x |
| | 5.5 | | ○ | ○ | ○ | ○ |
| | 6.0 | | ○ | ○ | ○ | ○ |
| | 6.5 | | ○ | ○ | ○ | ○ |
| | 7.0 | | ○ | ○ | ○ | ○ |
| | 7.5 | | Zirconia has a low relative density | | | |
| 1.0 | 4.5 | | ○ | ○ | x | x |
| | 5.0 | | ○ | ○ | x | x |
| | 5.5 | | ○ | ○ | ○ | ○ |
| | 6.0 | | ○ | ○ | x | x |
| | 6.5 | | Zirconia has a low relative density | | | |
| | 7.0 | | | | | |
| | 7.5 | | | | | |

TABLE 3

| Zirconia | | Alumina | | | | |
|---|---|---|---|---|---|---|
| Material grain size (μm) | Yttria (mol %) | Material grain size (μm) | Heating and cooling cycles (times) | | | |
| | | | 5,000 | 10,000 | 20,000 | 50,000 |
| 0.1 | 4.5 | 0.7 | ○ | ○ | x | x |
| | 5.0 | | ○ | ○ | ○ | ○ |
| | 5.5 | | ○ | ○ | ○ | ○ |
| | 6.0 | | ○ | ○ | ○ | ○ |
| | 6.5 | | ○ | ○ | ○ | ○ |

TABLE 3-continued

| Zirconia | | Alumina | | | | |
|---|---|---|---|---|---|---|
| Material grain size (μm) | Yttria (mol %) | Material grain size (μm) | Heating and cooling cycles (times) | | | |
| | | | 5,000 | 10,000 | 20,000 | 50,000 |
| | 7.0 | | o | o | x | x |
| | 7.5 | | Zirconia has a low relative density | | | |
| 0.5 | 4.5 | | o | o | x | x |
| | 5.0 | | o | o | o | x |
| | 5.5 | | o | o | o | o |
| | 6.0 | | o | o | o | o |
| | 6.5 | | o | o | o | o |
| | 7.0 | | o | o | o | o |
| | 7.5 | | Zirconia has a low relative density | | | |
| 1.0 | 4.5 | | o | x | x | x |
| | 5.0 | | o | o | x | x |
| | 5.5 | | o | o | o | o |
| | 6.0 | | o | o | o | o |
| | 6.5 | | Zirconia has a low relative density | | | |
| | 7.0 | | | | | |
| | 7.5 | | | | | |

What is claimed is:

1. A multilayered air-fuel ratio sensing element comprising a zirconic solid electrolytic body and a heat-generating portion equipped with a heater, wherein said zirconic solid electrolytic body is made of a partially stabilized zirconia containing 5 to 7 mol % yttria and having a mixed phase structure including a cubic phase, monoclinic phase and a tetragonal phase, said zirconic solid electrolytic body has a relative density of 94 to 100% with a mean sintered grain size of 0.5 to 3.0 μm, said heat-generating portion includes an alumina substrate which is located adjacent to said zirconic solid electrolytic body and has a relative density of 95 to 100% with a mean sintered grain size of 0.5 to 4.0 μm, and said partially stabilized zirconia has an M/C ratio in a range from 0.05 to 0.25, the M/C ratio being defined by the following equation:

$$\frac{M}{C} = \frac{M(111) + M(11\bar{1})}{M(111) + M(11\bar{1}) + C(111)}$$

wherein $M(11\bar{1})$ represents a reflective integrated intensity of a monoclinic phase $(11\bar{1})$, $M(111)$ represents a reflective integrated intensity of a monoclinic phase (111), and $C(111)$ represents a reflective integrated intensity of a cubic phase (111), wherein a thermal expansion difference Δ between said alumina substrate and said partially stabilized zirconia is in a range from 0 to 0.2, said thermal expansion difference Δ being defined by the following equation:

$$\Delta = \frac{C_{ZR} \cdot T - C_{AL} \cdot T}{1 + C_{AL} \cdot T} \times 100\%$$

wherein $C_{ZR}$ represents a thermal expansion coefficient of the partially stabilized zirconia in a temperature range from room temperature to 1,000° C.; $C_{AL}$ represents a thermal expansion coefficient of the alumina in a temperature range from room temperature to 1,000° C.; and T represents the temperature variation from room temperature to 1,000° C., and wherein a ratio of the mean sintered grain size of said alumina substrate to the mean sintered grain size of said zirconic solid electrolytic body is in a range from 0.33 to 4.00.

2. The multilayered air-fuel ratio sensing element in accordance with claim 1, wherein said heat-generating portion includes a first alumina substrate, a second alumina substrate, and a third alumina substrate, said heater is interposed between said first alumina substrate and said second alumina substrate, and said third alumina substrate is located adjacent to said zirconic solid electrolytic body.

3. The multilayered air-fuel ratio sensing element in accordance with claim 1, wherein said heat-generating portion includes a first alumina substrate and a second alumina substrate, said heater is interposed between said first alumina substrate and said second alumina substrate, and said second alumina substrate is located adjacent to said zirconic solid electrolytic body.

4. The multilayered air-fuel ratio sensing element in accordance with claim 3, wherein said zirconic solid electrolytic element has a measuring electrode facing a measuring gas chamber at one surface thereof, and said zirconic solid electrolytic element has a reference electrode facing a reference chamber at an opposed surface thereof.

* * * * *